United States Patent [19]

Lamb

[11] 3,970,760

[45] July 20, 1976

[54] FUNGITOXIC COMPOSITIONS CONTAINING 2,2'-DIHYDROXYDINAPHTHYLMETHANE

[75] Inventor: Glentworth Lamb, Trenton, N.J.

[73] Assignee: American Cyanamid Company, Stamford, Conn.

[22] Filed: Dec. 20, 1972

[21] Appl. No.: 317,043

[52] U.S. Cl. .............................................. 424/346
[51] Int. Cl.² ........................................... A01N 9/26
[58] Field of Search .................................. 424/346

[56] References Cited
UNITED STATES PATENTS
3,389,685  6/1968  MacPhee .............................. 119/3

OTHER PUBLICATIONS

Gump et al., J. Soc. Cosmetic Chemists 11, 307–314 (1960).

Primary Examiner—Albert T. Meyers
Assistant Examiner—Allen J. Robinson
Attorney, Agent, or Firm—Harry H. Kline

[57] ABSTRACT

There is provided a novel preparation for the control of fungi in which a major amount of an inert fungicidal carrier and a minor amount of 2,2'-dihydroxydinaphthylmethane are admixed.

1 Claim, No Drawings

FUNGITOXIC COMPOSITIONS CONTAINING 2,2'-DIHYDROXYDINAPHTHYLMETHANE

This invention relates to improved fungicidal compositions. More particularly, it relates to new fungicidal compositions containing 2,2'-dihydroxydinaphthylmethane as the active ingredient. The invention is also concerned with methods for protecting agricultural, organic and related articles from attack by microorganisms.

A plethora of fungicides are known. However, many are relatively expensive to manufacture. If a fungicide which is effective, inexpensive and relatively simple to make could be devised, such would serve a long felt need in the art.

According to the present invention, compositions containing 2,2'-dihydroxydinaphthylmethane have been found to possess unusual fungicidal properties. These compositions are particularly effective in preventing and retarding fungus growth on plant tissues and other organic matter.

Advantageously, 2,2'-dihydroxydinaphthylmethane is relatively inexpensive and is readily synthesized. Methods for its preparation are known in the art. For instance, one such method involves the reaction of β-naphthol with formaldehyde in the presence of sodium hydroxide.

In general, it is preferred to incorporate 2,2'-dihydroxydinaphthylmethane in a variety of suitable carriers or diluents. As one advantage of the invention, the fungicidal compound is effective in dilute concentrations. Such composition can be prepared as a solution by dissolving it in a water/acetone or alcohol mixture. It can also be prepared either as a suspension in a suitable non-solvent or as a dust. Suspensions or dispersions in a carrier, such as water, are quite useful in the treatment of plant foliage. The active compound may also be conveniently applied to foliage by the aerosol method. In the latter utilization, the active compound can be directly dissolved in a highly volatile liquid carrier, such as dichlorodifluoromethane, under pressure, or the compound can be dissolved in a lesser volatile solvent, such as benzene, and this solution admixed with a highly volatile liquid aerosol carrier.

Fungicidal dusts may be prepared by mixing the active compound with dusting materials as for example clay, pyrophyllite, pumice, fuller's earth and bentonite. Thus, seed can be protected from soil organisms by incorporating the active compound into a solid carrier while admixing seeds with the fungicidal composition as by tumbling.

Although a wide weight range of fungicidal compound to inert carrier or diluent and up to 25% may be used, it has been found that a percentage range of from about 0.01% to about 10% of active ingredient, and preferably 0.4% is adequate for most aqueous dispersion preparations. However, in a dust composition, not more than about 10% of active ingredient is satisfactory for most applications.

The composition of the present invention may advantageously contain any compatible commercially available dispersing agent for the fungicidal compounds when they are employed in an aqueous suspension. Illustrative examples of such dispersing or surface active agents include: the fatty acid esters of polyhydric alcohols, the sodium salt of polymerized propylnaphthalene sulfonic acid, as for instance, surface active compounds formed by condensing formaldehyde with propyl naphthalene sodium sulfonate, the alkylaryl polyether alcohols, and the ethylene oxide addition products of the latter. Usually, from one to five parts per hundred parts of fungicide is a good operating range.

While the fungicidal composition of the present invention can be used as a powder or in liquid composition, other active ingredients may be added thereto to prepare a multi-purpose preparation. Such other active ingredients can be added as the carrier per se or, in addition, an inert carrier can also be used. These active ingredients in admixture can be parasiticides, fertilizers and the like. Thus, an effective dose of the 2,2'-dihydroxydinaphthylmethane compound and an insecticide, such as parathion or malathion, can be employed as a multi-purpose preparation.

The invention will be illustrated in conjunction with the following examples which are to be taken as illustrative only and not by way of limitation. All parts are by weight, unless otherwise noted.

EXAMPLE 1

This example illustrates the preparation of 2,2'-dihydroxydinaphthylmethane.

To a suitable reaction vessel are added to 85 parts of sodium hydroxide in flake form and 1,200 parts of β-naphthol flakes. The latter mixture is admixed with 945 parts of anhydrous alcohol at temperatures below 50°C. Paraformaldehyde (62.5 parts) is added with stirring and the overall mixture is heated at 70° - 80°C. for 2 hours. There is next recovered 2,2'-dihydroxydinaphthylmethane in good purity.

EXAMPLE 2

The foliage of (a) Bonnie Best tomato plants with four true leaves, (b) Early Marketer cucumber plants with two true leaves, and (c) Nato variety rice was each sprayed to run off with 50/50 acetone/water solution of 2,2'-dihydroxydinaphthylmethane at rates of 100 ppm and 500 ppm. The plants are dried and then sprayed with a mixed inoculum of late blight (*Phytophthora infestans*), anthracnose (*Colletotrichum lagenarium*), and blast (*Piricularia oryzae*). The plants are immediately placed in a constant temperature cabinet at 62°F. and a saturated atmosphere. After 24 hours, the temperature is advanced to 70°F. and there held for 72 hours. The plants are then stored in a greenhouse. Readings on disease control are made seven days after inoculation.

The data obtained are recorded in the Table below in which 5 means no disease, 4 is a trace, and 0 is the disease as seen on the untreated plant.

TABLE I

| Compound | Disease Control at rates in ppm | | | | | |
| --- | --- | --- | --- | --- | --- | --- |
| | 100 | | | 500 | | |
| | CA[1] | LB[2] | NR[3] | CA[1] | LB[2] | NR[3] |
| 2,2'-dihydroxydinaphthylmethane | 5 | 4 | 5 | 5 | 4 | 5 |
| Control (acetone/water — 50/50) | 0 | 0 | 0 | 0 | 0 | 0 |

CA[1] is cucumber anthracnose
LB[2] is late blight of tomato
NR[3] is Nato variety of rice Similar results are attained when the active ingredient is employed as a wettable powder by blending and milling 70 parts of 2,2'-dihydroxydinaphthylmethane, 22 parts of kaolin clay, 1 part of carboxymethylcellulose, and 2 parts of alkylarylpolyether alcohol to an average particle size of three microns. A 70% aqueous solution is next prepared and applied to the host plants following the procedure of the above example.

I claim:

1. A method for the protection of plant materials susceptible to attack by fungi which comprises: applying to the said plant materials a preparation comprising from about 99.99% to about 90% of an inert solid fungicidal carrier selected from the group consisting of clay, pumice, fuller's earth, pyrophyllite and bentonite, and from about 0.01% to about 10% of 2,2'-dihydroxydinaphthylmethane, said preparation being applied to said plant materials at a rate ranging from about 100 ppm to about 500 ppm of said 2,2'dihydroxydinaphthylmethane.

* * * * *